(12) United States Patent
Kuramori et al.

(10) Patent No.: US 9,549,686 B2
(45) Date of Patent: Jan. 24, 2017

(54) METHOD, APPARATUS, AND PROGRAM FOR EVALUATING DRIVABILITY OF A VEHICLE

(75) Inventors: Akira Kuramori, Hiratsuka (JP); Masayoshi Kamijo, Ueda (JP); Tsugutake Sadoyama, Ushiku (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 1127 days.

(21) Appl. No.: 12/440,395

(22) PCT Filed: Sep. 7, 2007

(86) PCT No.: PCT/JP2007/067514
§ 371 (c)(1),
(2), (4) Date: Mar. 6, 2009

(87) PCT Pub. No.: WO2008/032656
PCT Pub. Date: Mar. 20, 2008

(65) Prior Publication Data
US 2010/0179764 A1 Jul. 15, 2010

(30) Foreign Application Priority Data
Sep. 11, 2006 (JP) ................... 2006 245377

(51) Int. Cl.
*G06F 19/00* (2011.01)
*A61B 5/0488* (2006.01)
(Continued)

(52) U.S. Cl.
CPC ............ *A61B 5/0488* (2013.01); *B60W 40/08* (2013.01); *G01M 17/06* (2013.01); *A61B 5/18* (2013.01); *A61B 5/6893* (2013.01)

(58) Field of Classification Search
CPC ........ G01M 17/06; A61B 5/0488; A61B 5/18; A61B 5/6893; B60W 40/08
(Continued)

(56) References Cited

U.S. PATENT DOCUMENTS 4,592,673 A * 6/1986 Lee ........................... E01C 1/04
404/1
5,372,050 A * 12/1994 Shinki et al. .............. 74/473.31
(Continued)

FOREIGN PATENT DOCUMENTS

JP 2002-214083 7/2002
JP 2004-345482 12/2004
JP 2005-87485 4/2005

OTHER PUBLICATIONS

PCT/JP2007/067514 International Search Report, Oct. 9, 2007.

*Primary Examiner* — Jermele M Hollington
*Assistant Examiner* — Haidong Zhang
(74) *Attorney, Agent, or Firm* — Knobbe Martens Olson & Bear LLP

(57) ABSTRACT

A time series myoelectric potential signal is acquired, which is representative of time series activity amount of a muscle of a driver when the driver is performing a driving operation on the vehicle, the muscle being involved in the driving operation. Based on the acquired time series myoelectric potential signal, a parameter value indicative of a fluctuation amount of the time-series myoelectric potential signal and an average value of the myoelectric potential signal are obtained. Drivability of the vehicle is evaluated based on the obtained parameter value and the obtained average value.

8 Claims, 13 Drawing Sheets

(51) Int. Cl.
  *B60W 40/08* (2012.01)
  *G01M 17/06* (2006.01)
  *A61B 5/18* (2006.01)
  *A61B 5/00* (2006.01)

(58) Field of Classification Search
  USPC ...... 340/438, 439, 575, 576; 701/42, 46, 70, 701/72, 300; 702/19
  See application file for complete search history.

(56) References Cited

U.S. PATENT DOCUMENTS

2005/0080350 A1\* 4/2005 Kuramori et al. ............ 600/546
2005/0090757 A1\* 4/2005 Kuramori et al. ............ 600/546
2006/0073894 A1\* 4/2006 Kuramori et al. ............. 463/36

\* cited by examiner (a)

(b)

(c)

(a)

(b)

(c)

(a)

(b)

(c)

(a)

(b)

(c)

METHOD, APPARATUS, AND PROGRAM FOR EVALUATING DRIVABILITY OF A VEHICLE

This application is the U.S. National Phase under 35. U.S.C. §371 of International Application PCT/JP2007/067514, filed Sep. 7, 2007, which claims priority to Japanese Patent Application No. 2006-245377, filed Sep. 11, 2006. The International Application was published under PCT Article 21(2) in a language other than English.

TECHNICAL FIELD

The present invention relates to a method, an apparatus, and a program for evaluating drivability of a vehicle.

BACKGROUND ART

At present, in an evaluation of characteristics of a driver who drives an automobile vehicle or of drivability of an automobile vehicle, or in performing an operation assist control for assisting an operation performed by a driver who drives an automobile vehicle to thereby control a behavior of the automobile vehicle, information on the automobile vehicle being driven or biological information of the driver who is driving the vehicle are used.

Of those, the drivability of an automobile vehicle is determined based on a balance between two contradictory types of performance such as responsiveness and stability. The responsiveness herein refers to an index for indicating how sensitively the steering state of an automobile vehicle reacts to the operation (for example, steering operation) performed by the driver. When the vehicle is high in responsiveness, the vehicle can be steered greatly even when the driver performs the operation by a significantly light force. Similarly, the stability refers to an index for indicating a degree of insusceptibility of the steering state of an automobile vehicle with respect to an influence due to a disturbance resulting from a road surface irregularity or the like. When the vehicle is high in stability, the vehicle can travel in a stable steering state even when affected by a great disturbance resulting from the road surface irregularity or the like, without the need for a great steering adjustment force to be exerted by the driver driving the vehicle. As has been widely recognized in general, a vehicle which is too high in responsiveness tends to be low in stability, while a vehicle which is too high in stability tends to be low in responsiveness. The drivability of an automobile vehicle, which is determined by the two contradictory types of performance such as the responsiveness and the stability, is difficult to quantify. Conventionally, in order to quantitatively evaluate the drivability of an automobile vehicle, a feeling test has been mainly conducted to make the evaluation. In the feeling test, a driver who drives a vehicle of evaluation target quantitatively evaluates the vehicle of evaluation target in terms of drivability thereof, based on the feeling of the driver oneself.

As regards the feeling test which has been conventionally conducted, Patent Document 1 described below, for example, discloses an apparatus for measuring driving stability of a vehicle, which has been made for the purpose of appropriately evaluating the driving stability of a vehicle based on a quantitative index. Patent Document 1 describes that attention is focused on how the steering operation performed by a driver is affected by external work resulting from a road surface irregularity or the like, and the driving stability is evaluated by using as an index a steering work ratio, which is obtained as a product of a time differential value of a steering angle (steering speed) and a steering force. Patent Document 1 describes that the steering work ratio corresponds to the amount of work externally received due to a road surface irregularity or the like. Further, in particular, in the case where the steering work ratio has a negative value, the wheel steering speed (time differential value of a steering angle) is mutually opposite in direction to the wheel steering force, and accordingly the case is regarded as a state where the driver is trying to stop the movement of the steering wheel and is externally receiving work resulting from a road surface irregularity or the like. In Patent Document 1 described below, the driving stability of a vehicle can be evaluated according to the magnitude of the negative steering work ratio.

Patent Document 1: JP 2002-214083 A

DISCLOSURE OF THE INVENTION

Problems to be Solved by the Invention

According to the apparatus disclosed in Patent Document 1, a torque amount between the steering wheel and the wheel or a myoelectric potential of the driver is detected, and the magnitude of the torque amount or of the myoelectric potential is regarded as being corresponding to an amount of a steering force applied to the steering wheel of the vehicle by the driver. Then, further, the steering angle of the steering wheel is detected by a steering angle detecting means, and the driving stability of the vehicle is evaluated based on the detected steering force (torque amount or myoelectric potential) and the detected steering angle. In the case where the steering work ratio is used as an index to evaluate the driving stability as in the case of the apparatus disclosed in Patent Document 1, it is necessary to provide two means (such as sensors) including means for detecting a steering force and means for detecting a steering angle, which requires a relatively great deal of cost. In this case, the information on the steering force relates to information on a driver, and can be obtained by measuring the myoelectric potential of the driver as described above. On the other hand, the steering speed (rpm) (steering angle) relates to information on the vehicle, and therefore it is necessary to provide a sensor such as a steering angle sensor to the vehicle in order to obtain the information. According to the vehicle driving stability evaluating apparatus disclosed in Patent Document 1, the driving stability cannot be evaluated unless the vehicle is provided with, for example, a steering angle sensor, as described above. According to the apparatus disclosed in Patent Document 1, for example, in the case of evaluating the vehicle driving stability of any measurement target vehicle which is not provided with, for example, a steering angle detecting means (such as a steering angle sensor), it is necessary to provide the measurement target vehicle with the steering angle detecting means in advance before starting the driving stability evaluation, which has resulted in a great increase in time and cost necessary for the evaluation.

The present invention has been made in view of the above-mentioned problems, and it is an object of the present invention to provide a method, an apparatus, and a program for quantitatively evaluating drivability of an arbitrary vehicle with ease and accuracy.

To solve the above mentioned problems, the present invention provides a method of evaluating drivability of a vehicle, comprising the steps of: acquiring a time-series myoelectric potential signal of a muscle of a driver when the driver is performing a driving operation on the vehicle, the muscle being involved in the driving operation; obtaining, based on the acquired time-series myoelectric potential signal, a parameter value representing a fluctuation amount of the time-series myoelectric potential signal; and evaluating, based on the parameter value, the drivability of the vehicle.

In the invention, the time-series myoelectric potential signal preferably corresponds to information on a surface myoelectric potential of a muscle involved in the driving operation; and in obtaining the parameter value, the parameter value is preferably obtained based on a waveform obtained by rectifying and smoothing the information on a surface myoelectric potential.

It is also preferable the parameter value comprises at least one of a standard deviation, a dispersion, a distribution range of the time-series myoelectric potential signal, and a root mean square of the waveform obtained by subjecting the information corresponding to the time-series myoelectric potential signal to time differentiation.

Preferably, a mean value of the time-series myoelectric potential signal is obtained together with the parameter value; and in evaluating the drivability, the drivability of the vehicle is evaluated based on both the parameter value and the mean value.

Then, the mean value preferably comprises at least one of an arithmetic mean value and a root mean square of the time-series myoelectric potential signal.

Preferably, the parameter value is obtained by using a myoelectric potential signal corresponding to a time during which the vehicle is traveling under a predetermined traveling condition; and the predetermined traveling condition comprises a condition that the vehicle travels on a traveling path which at least includes a curved path having a constant curvature.

Preferably, in obtaining the parameter value, the parameter value is obtained by using a myoelectric potential signal corresponding to a time during which the vehicle is traveling under the predetermined traveling condition; and the predetermined traveling condition is a condition that the vehicle travels on a curved path having a constant curvature.

The predetermined traveling condition may further comprise a condition that the vehicle travels at a constant traveling speed.

It is preferable that the muscle involved in the driving operation includes at least one of a muscle for operating a steering unit of the vehicle, a muscle involved in keeping a posture of the driver driving the vehicle, and a muscle for operating a speed controlling unit of the vehicle.

The present invention also provides an apparatus for evaluating drivability of a vehicle, comprising: means for acquiring a time-series myoelectric potential signal of a muscle of a driver when the driver is performing a driving operation on the vehicle, the muscle being involved in the driving operation; means for obtaining, based on the acquired time-series myoelectric potential signal, a parameter value representing a fluctuation amount of the time-series myoelectric potential signal; and means for evaluating, based on the parameter value, the drivability of the vehicle.

The present invention still also provides a program executed in an apparatus for evaluating drivability of a vehicle, the program causing a computer to execute the steps of: acquiring a time-series myoelectric potential signal of a muscle of a driver when the driver is performing a driving operation on the vehicle, the muscle being involved in the driving operation; obtaining, based on the acquired time-series myoelectric potential signal, a parameter value representing a fluctuation amount of the myoelectric potential signal; and evaluating, based on the parameter value, the drivability of the vehicle.

Effects of the Invention

According to the present invention, the drivability of an arbitrary vehicle can be quantitatively evaluated with accuracy, based merely on the information related to the driver, that is, the time-series myoelectric potential signal of the driver. With the use of the method and the apparatus of the present invention, it is possible to evaluate the drivability of an arbitrary vehicle in a relatively short time and at relatively low cost. Further, as a traveling condition of a vehicle, a condition that the vehicle travels on a traveling path which includes a cornering path having a constant curvature is set, and the myoelectric potential signal of a muscle of the driver, the muscle being involved in a driving and steering operation of the vehicle, is obtained in time series in a state where the vehicle is traveling on the cornering path having a constant curvature. In the state where the vehicle is traveling on the cornering path having a constant curvature, the muscle involved in the driving and steering operation is exerting a substantially constant muscle force, with the result that the ratio of unnecessary noise component magnitude included in the myoelectric potential signal can be reduced. According to the present invention, the drivability of a vehicle can be obtained with accuracy based on the myoelectric potential signal which is low in ratio of noise component magnitude, and it is possible to accurately compare, for example, a plurality of vehicle specifications in terms of drivability even when the characteristic difference between the specifications is small. For example, tires of different specifications are attached to the same vehicle, and the drivability of the vehicle can be comparatively and quantitatively evaluated for each of the cases where the tires of different specifications are attached to the vehicle.

Figure 1:
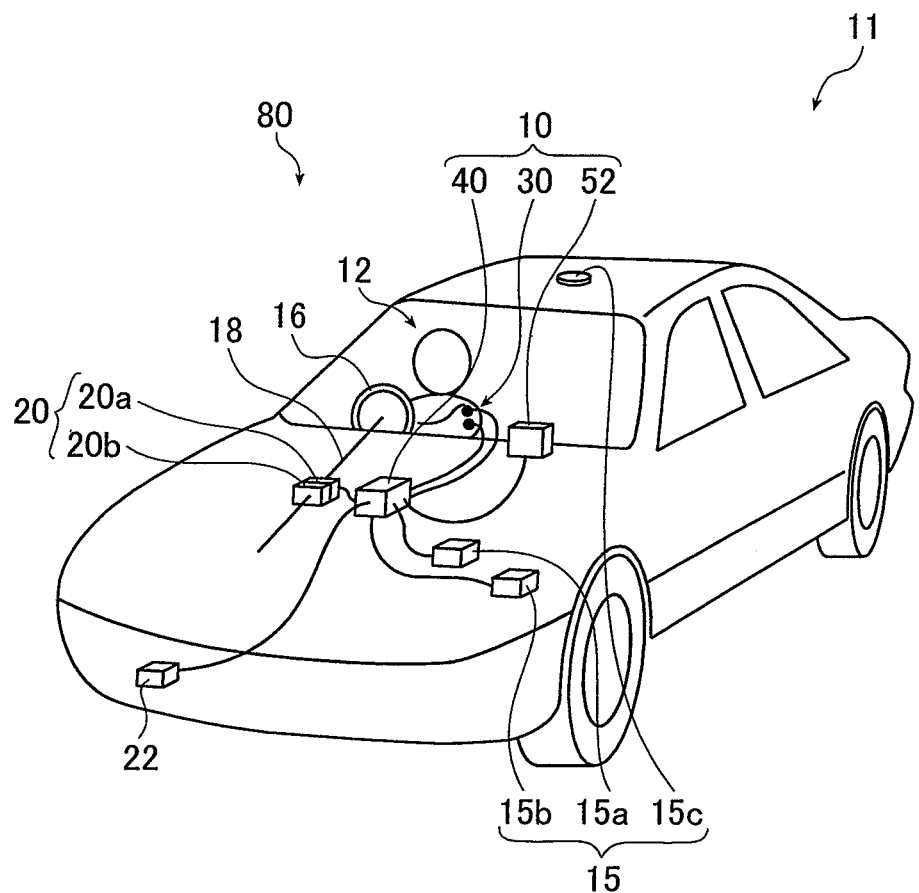
FIG. 1 A schematic block diagram illustrating a vehicle provided with an apparatus according to the present invention.

DESCRIPTION OF SYMBOLS 10 evaluating apparatus
11 vehicle
12 driver
15 first vehicle sensor
15a yaw rate sensor
15b vehicle speed sensor
15c GPS sensor
16 steering wheel
18 steering shaft
20 second vehicle sensor
20a steering angle sensor
20b steering torque sensor
22 third vehicle sensor
30 measuring unit
32, 34 detection sensor
36 electrode
38 amplifier
40 data processing unit
42 acquiring unit
43 memory
44 processing unit
45 CPU
46 calculating unit
48 evaluating unit
52 monitor

BEST MODE FOR CARRYING OUT THE INVENTION

Hereinbelow, a method, an apparatus, and a program for evaluating drivability of a vehicle according to the present invention will be described in detail based on a preferred embodiment with reference to the accompanying drawings. FIG. 1 is a schematic block diagram for illustrating a vehicle 11 provided with the apparatus of the present invention. The vehicle 11 is provided with an evaluating apparatus 10 which acquires a myoelectric potential signal of a muscle of a driver 12 who performs a driving operation of the vehicle 11, the muscle being involved in the driving operation, and evaluates the drivability of the vehicle 11 based on the acquired myoelectric potential signal.

The vehicle 11 is further provided with a first vehicle sensor 15 for acquiring information on behavior of the vehicle 11 corresponding to the operation of the driver 12. The first vehicle sensor 15 includes, for example, a yaw rate sensor 15a for detecting yawing behavior around a yawing axis of the vehicle 11, a vehicle speed sensor 15b for detecting a vehicle speed of the vehicle 11, and a GPS sensor 15c for detecting the location of the vehicle 11. The vehicle 11 is also provided with a second vehicle sensor 20 which includes a steering angle sensor 20a and a torque sensor 20b. The steering angle sensor 20a detects a rotational angle (steering angle) of a steering wheel 16, the rotational angle being generated when the driver 12 turns the steering wheel 16 which is axially supported by a steering shaft 18 of the vehicle 11. The steering torque sensor 20b detects a torque around the axis of the steering shaft 18, the torque being generated by the driving operation (rotating operation of steering wheel) performed by the driver 12. The vehicle 11 is also provided with a third vehicle sensor 22 for determining a condition of a traveling path ahead of the vehicle 11 (as to whether traveling path is straight or curved). The third vehicle sensor 22 includes, for example, a known photoelectronic sensor, by which light from reflecting plates disposed along a traveling path on which the vehicle 11 is to travel is detected, and a condition of the traveling path ahead of the vehicle 11 is determined by identifying a location of each of the reflecting plates according to the detection result. The information acquired by each of the first vehicle sensor 15, the second vehicle sensor 20, and the third vehicle sensor 22 is used for examining vehicle behavior in the evaluation of the drivability of the vehicle.

Figure 2:
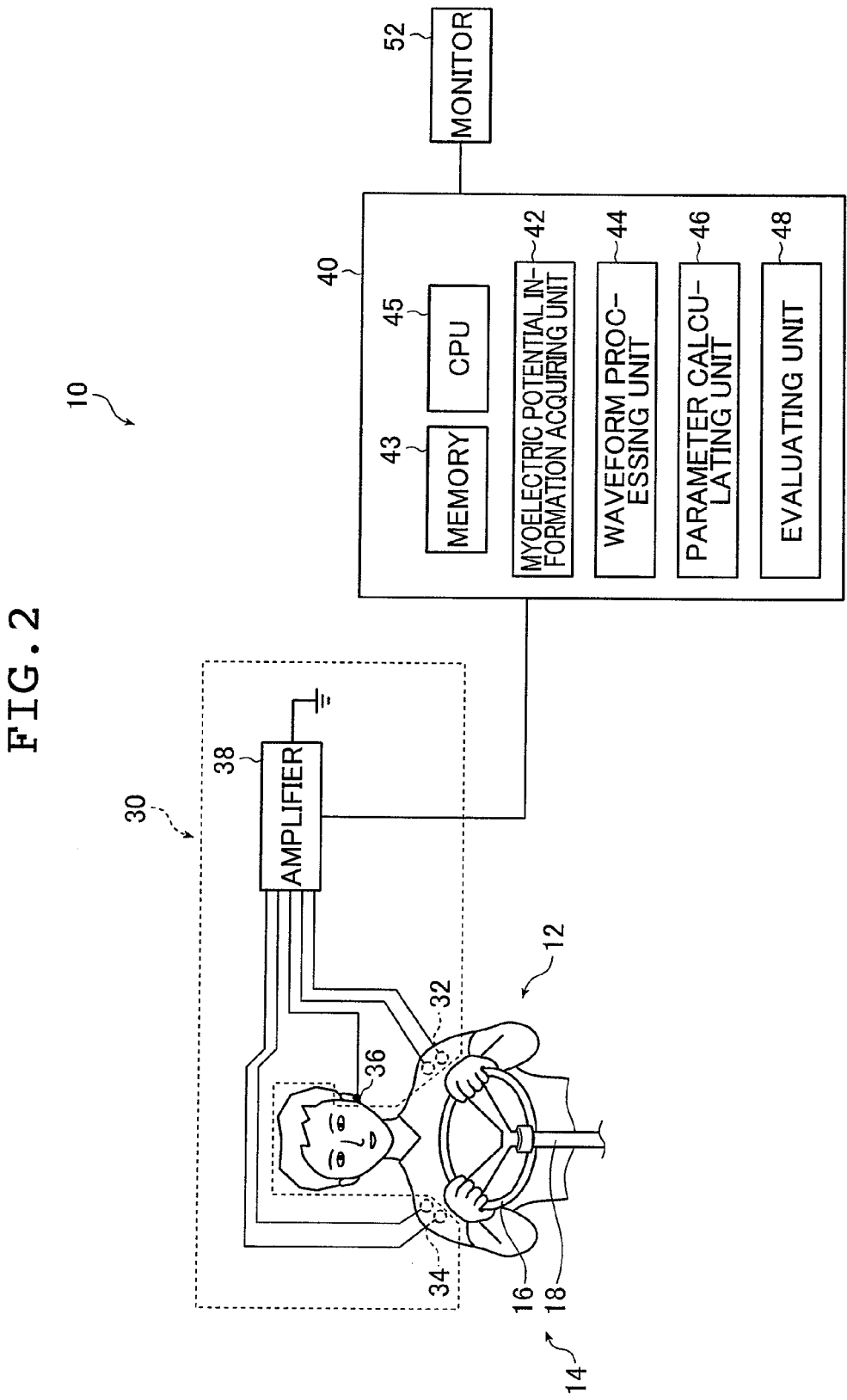
FIG. 2 A schematic block diagram illustrating an example of the apparatus of the present invention.

FIG. 2 is a schematic block diagram illustrating the evaluating apparatus 10 provided to the vehicle 11, which is an example of the apparatus of the present invention. The evaluating apparatus 10 is configured by including a measuring unit 30 for measuring, in time series, a myoelectric potential signal of a muscle involved in driving operational work conducted by the driver 12 who drives the vehicle, and a data processing unit 40. FIG. 2 is a diagram for illustrating an embodiment in which the apparatus of the present invention is used for evaluating drivability of a vehicle based on the time-series myoelectric potential signal. In the embodiment shown in FIG. 2, as the myoelectric potential signal, a myoelectric potential signal of a deltoid muscle is obtained, the deltoid muscle being one of the first muscles for operating a steering means such as a steering, of the muscles involved in the driving operation work.

Examples of the first muscles include, in addition to the deltoid muscle, a deltoid muscle, a supraspinatus muscle, an infraspinatus muscle, a teres minor muscle, a teres major muscle, and a subscapular muscle, which are located in a region of upper limb of the driver. Examples of the first muscles also include, for example, a biceps brachii muscle, a coracobrachial muscle, and a brachial muscle, which are located in an upper arm (anterior group). Also, a triceps brachii muscle located in an upper arm (posterior group) is included. A greater pectoral muscle, a smaller pectoral muscle, and an anterior serratus muscle, which are located in a chest region, are also included. According to the present invention, a myoelectric potential signal of any of the above-mentioned first muscles may be used for evaluating the drivability of a vehicle.

The measuring unit 30 is configured by including detection sensors 32 and 34 each for detecting, in time series, a myoelectric potential of the driver 12, an electrode 36, and an amplifier 38 for amplifying the myoelectric potentials from the detection sensors 32 and 34. The detection sensors 32 and 34 each detect, in time series, a myoelectric potential which indicates an activity amount of the first muscle of the driver 12. In this embodiment, as the myoelectric potential indicating the activity amount of the first muscle, a surface myoelectric potential of the deltoid muscle of the driver 12 is detected. The deltoid muscle is one of the muscles (first muscles) for operating a steering means such as a steering, which contributes to the rotating operation of the steering wheel 16 axially supported by the steering shaft 18 and is activated in relatively large motion when performing a steering operation of the vehicle. The surface myoelectric potential of the deltoid muscle of the driver 12 represents well enough degree of activity of the deltoid muscle in the steering operation of the vehicle 11 performed by the driver 12.

The detection sensor 32 is a sensor for detecting a surface myoelectric potential (myoelectric potential) of a deltoid muscle on the left shoulder of the driver 12, which is configured by including a pair of Ag/AgCL dish-shaped electrodes. The pair of dish-shaped electrodes are attached, as being spaced apart from each other by a predetermined distance of several mm, for example, 5 mm, to a surface of the left shoulder at which the deltoid muscle is located.

The detection sensor 34 is a sensor for detecting a surface myoelectric potential (myoelectric potential) of a deltoid muscle on the right shoulder of the driver 12, which is configured by including, similarly to the detection sensor 32, a pair of Ag/AgCL dish-shaped electrodes. The pair of dish-shaped electrodes are attached, as being spaced apart from each other by a predetermined distance of several mm, for example, 5 mm, to a surface of the left shoulder at which the deltoid muscle is located.

It should be noted that the electrodes of the detecting sensors 32 and 34 are not limited to Ag/AgCl electrodes, and may be formed of any other material such as Ag or stainless steel.

Figure 3:
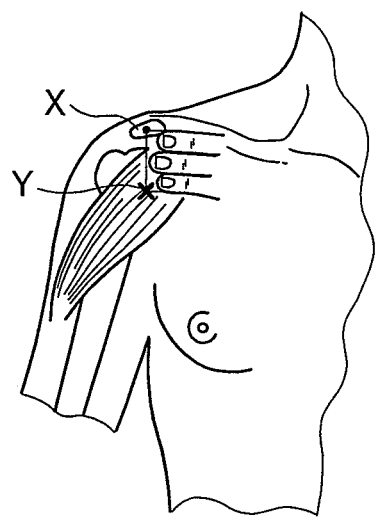
FIG. 3 A diagram illustrating where on a driver to attach a detection sensor of the evaluating apparatus shown in FIG. 2.

Before the electrodes are attached to the skin surface of the driver, the skin surface is scrubbed and cleaned by using alcohol. The electrodes are attached through an electrode paste. At this time, the skin surface is cleaned enough to have a reduced electric resistance of equal to or less than 30 k$\Omega$ (preferably 5 k$\Omega$). The two electrodes are attached to the bellies of a muscle to be measured so as to be in parallel with the muscle fibers. The electrodes are attached as being spaced apart from each other at a predetermined distance, at a position Y, as shown in FIG. 3, which is spaced apart from an outer end X of the clavicle by the width of three fingers in a longitudinal direction of the arm.

It should be noted that, according to this embodiment, the detection sensors are each attached to each of the right and left deltoid muscles of the driver 12, respectively. However, according to the apparatus and method of the present invention, in a case where, for example, a traveling path on which the vehicle 11 is to travel according to the driving operation of the driver 12 is already known and which of the right or left muscles to act positively is already known, the detection sensor may be attached to only one of the muscles which acts positively.

Figure 4:
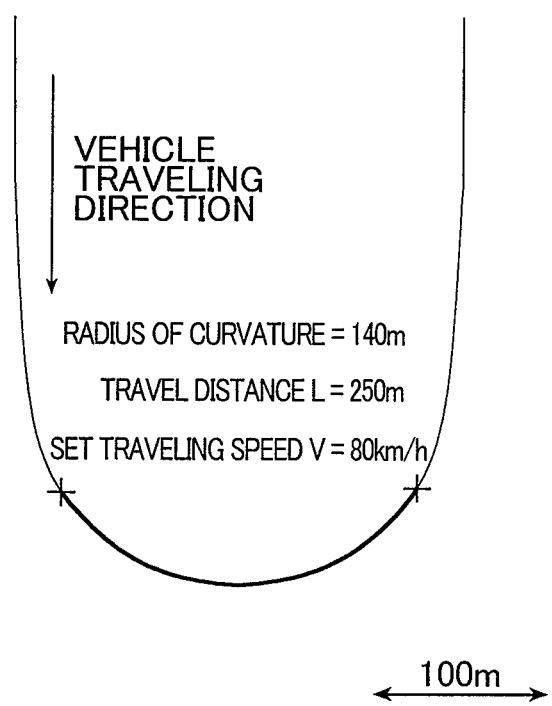
FIG. 4 An example of a condition set for a traveling path on which a vehicle travels, according to a method of the present invention.

FIG. 4 is an example of a condition set for a traveling path on which the vehicle 11 travels, which is used in the method of the present invention performed by using the evaluating apparatus 10 shown in FIG. 1. According to the method of the present invention, it is preferable to set in advance a traveling condition in terms of, for example, a traveling path on which a vehicle is to travel and vehicle speed of traveling. According to the condition illustrated in FIG. 4, the vehicle 11, which has traveled on a straight path, gradually increases a steering angle so as to enter a curved path having a constant curvature, passes through the curved path having a constant curvature, and again travels straightforward. According to the method of the present invention, the myoelectric potential signal of a muscle positively contributing to the steering operation may be obtained in a time range (evaluation time range to be described later) indicated by the bold line in FIG. 4, during which the vehicle is passing through the curved path portion having a constant curvature. In a state where the vehicle is traveling on the curved path having a constant curvature, it can be said that the above-mentioned first muscle is exerting a substantially constant muscle force in order to maintain the steering wheel at a substantially constant steering angle. In a state where the first muscle is exerting a substantially constant muscle force, it is possible to reduce a ratio of unnecessary noise components included in the myoelectric potential signal. Further, in a state where the vehicle is traveling on a curved path having a constant curvature, the first muscle is exerting a substantially constant muscle force while a joint angle of the shoulder or the elbow of, for example, the front arm or the upper limb is maintained substantially constant. Accordingly, in a state where the vehicle is traveling on a curved path having a constant curvature, a change in a contact state of the electrodes, a change in a positional relation between the muscle under the skin and the electrodes, and fluctuations of a lead wire connecting the electrodes and the amplifier, and the like, are reduced, with the result that a noise in the myoelectric potential signal resulting therefrom is also reduced. Also, on the curved path having a constant curvature described above, a target line indicated to the driver is simple and clear, and even the driver is allowed to have a less amount of freedom in driving operation accordingly. As a result, the differences among the individual driving characteristics are minimized, which results in reduced variations among individuals. According to the present invention, for the purpose of reducing a ratio of unnecessary noise components included in the myoelectric potential signal so as to evaluate drivability of a vehicle with higher accuracy, and quantitatively comparing the evaluation results for respective drivers with accuracy, it is preferable to evaluate the drivability of a vehicle based on the myoelectric potential signal of a muscle positively contributing to the steering operation in the evaluation time range during which the vehicle is passing through the curved path having a constant curvature. According to the present invention, as the condition to be set for the traveling path on which a vehicle is to travel, it is preferable to set a condition that a vehicle passes through at least a curved path portion having a constant curvature.

According to the condition set for the traveling path as shown in FIG. 4, the vehicle 11 travels to turn to the left with respect to the traveling direction. At this time, it is assumed that the driver 12 performs the steering operation (rotates steering) by mainly using the deltoid muscle on the right side. In this case, the detection sensor may be attached only to the deltoid muscle on the right side. In the steering operation, it depends on the driver as to which one of the right and left muscles is mainly used, and therefore, the detection sensor may be attached to either one of the right and left muscles according to each driver. It should be noted that in a case where, for example, the traveling condition of the vehicle 11 has not been determined in detail and it has not been decided yet which one of the right and left muscles is subjected to myoelectric potential measurement for the evaluation of the drivability of the vehicle 11, the detection sensors may be attached to both of the right and left muscles. Also, in a case where information on an intensity of simultaneous activity of the right and left muscles is used for evaluating the drivability of a vehicle, which is to be described later, the detection sensors may be attached to both of the right and left muscles.

Meanwhile, the electrode 36 serves as an earth electrode, and is attached to the earlobe of the driver 12, which is an electrically inactive position, so as to maintain the potential of the driver 12 constant. The electrode 36 is provided so as to allow the detection sensors 32 and 34 to perform measurement precisely. The electrode 36 connected to the amplifier 38 is grounded via the amplifier 38. The amplifier 38 is a known operational amplifier for amplifying the myoelectric potentials detected by the detection sensors 32 and 34, and is connected to the detection sensors 32 and 34 via a lead wire. The myoelectric potentials, which have been detected by the detection sensors 32 and 34 and amplified, are transmitted to the data processing unit 40.

The data processing unit 40 is configured by including an acquiring unit 42, a processing unit 44, a calculating unit 46, and an evaluating unit 48. The data processing unit 40 may be a computer in which a CPU 45 executes programs stored in a memory 43 so as to function the units. Alternatively, the data processing unit 40 may be a dedicated device in which each of the units is formed of a dedicated circuit. The data processing unit 40 also has an input device connected thereto, which is not shown. An operator is capable of changing the evaluation time range, which is to be described later, or the like, by operating the input device.

The acquiring unit 42 acquires information on the myoelectric potentials detected by the detection sensors 32 and 34. The time-series myoelectric potential signal acquired by the acquiring unit 42 is transmitted to the processing unit 44. The processing unit 44 samples the received time-series myoelectric potential signal, and then subjects the signal to full-wave rectification. After that, the processing unit 44 smoothes the signal by using a smoothing filter (low-pass filter), to thereby obtain a smoothed signal waveform of the myoelectric potential (smoothed waveform) for each of the right and left deltoid muscles.

FIG. 5(a) shows an example of a time-series myoelectric potential signal of the right deltoid muscle of the driver 12, which has been acquired by the acquiring unit 42 when the vehicle 11 has been driven under the traveling condition shown in FIG. 4. FIG. 5(b) shows a signal waveform (smoothed waveform) of the myoelectric potential, which is obtained by processing the time-series myoelectric potential signal shown in FIG. 5(a) by the processing unit 44. The processing unit 44 subjects the time-series myoelectric potential signal shown in FIG. 5(a) to full-wave rectification, and then smoothes the signal by using a smoothing filter. An example of the smoothing filter includes a fifth-order low-pass filter having a cutoff frequency of 5 Hz. The evaluation target time range shown in each of FIGS. 5(a) and (b) corresponds to the time range during which the vehicle 11 is traveling on the curved path portion having a constant curvature (region indicated by bold line in FIG. 4). The myoelectric potential signal before being smoothed is a signal including a high-frequency component which is originally generated along with the contraction of the muscle. The processing unit 44 subjects the myoelectric potential signal to full-wave rectification before smoothing the signal, such that the myoelectric potential waveform satisfactorily corresponds to a force generated by the contraction of the muscle.

The calculating unit 46 obtains, based on the myoelectric waveform which has been subjected to full-wave rectification and then smoothed by the processing unit 44, a mean value (referred to as intensity reference value) of the myoelectric potentials of a muscle involved in the operation and a parameter value (referred to as fluctuation reference value) indicating a fluctuation amount of the myoelectric waveform in the above-mentioned evaluation time range.

In this case, the evaluation time range refers to a time range during which the vehicle is passing through the curved path portion having a constant curvature indicated by the bold line in FIG. 4. In the case where the condition regarding a traveling path on which the vehicle 11 is to travel and the condition regarding the traveling speed are determined in advance, the time range during which the vehicle 11 is traveling at a constant curvature can be defined in advance with respect to the starting time of traveling of the vehicle 11. In the case where, for example, the conditions in terms of a traveling path or the traveling speed are determined in advance, an operator may input the conditions related to the predetermined time range (evaluation time range) as described above by using an input means, which is not shown, connected to the data processing unit 40, and the memory 43 may store information on the evaluation range set as described above.

The evaluation time range corresponds to a time range during which the vehicle 11 is cornering according to the operation of the driver 12. The evaluation time range may preferably correspond to a time range during which a muscle to be subjected to myoelectric potential measurement is acting at a substantially constant intensity. Specifically, it is preferable that, in the time range, the vehicle 11 be cornering along a curved path having a constant curvature according to the operation of the driver 12, and it is more preferable that, in the time range, the vehicle 11 be cornering along a curved path having a constant curvature at a constant traveling speed. For this reason, the above-mentioned traveling condition preferably includes a condition that the vehicle travels on a curved path having a constant curvature, and further the condition preferably includes a condition that the vehicle travels on a curved path having a constant curvature at a constant traveling speed. Then, in a case where it is desired to set the evaluation time range in advance, the traveling speed is preferably set to a predetermined speed in advance.

It should be noted that in a case where the evaluation time range is stored in advance based on the traveling condition set in advance, it is necessary that the vehicle 11 be traveling in accordance with the traveling condition set in advance, in order that the evaluation time range may correctly correspond to the time range during which the vehicle 11 is cornering according to the operation of the driver 12. The calculating unit 46 may determine, based on the information acquired by the first vehicle sensor 15 (15a to 15c), whether the vehicle 11 is traveling in accordance with the traveling condition determined in advance. For example, the detection result obtained by the yaw rate sensor 15a may be used for judging whether the vehicle 11 is traveling on the curved path at a constant curvature. Alternatively, the detection result obtained by the vehicle speed sensor 15b may be used for judging whether the vehicle 11 is traveling at a predetermined traveling speed. Still alternatively, the detection result obtained by the GPS sensor 15c may be used for identifying the traveling speed or the traveling trajectory of the vehicle 11. In a case where the vehicle 11 is traveling without following the predetermined traveling condition, it is indicated that the vehicle 11 is traveling, in the evaluation time range stored in advance, not at a constant curvature or a predetermined constant speed. In this case, a warning screen may be displayed on, for example, a display 52, without calculating the fluctuation reference value.

Figure 6:
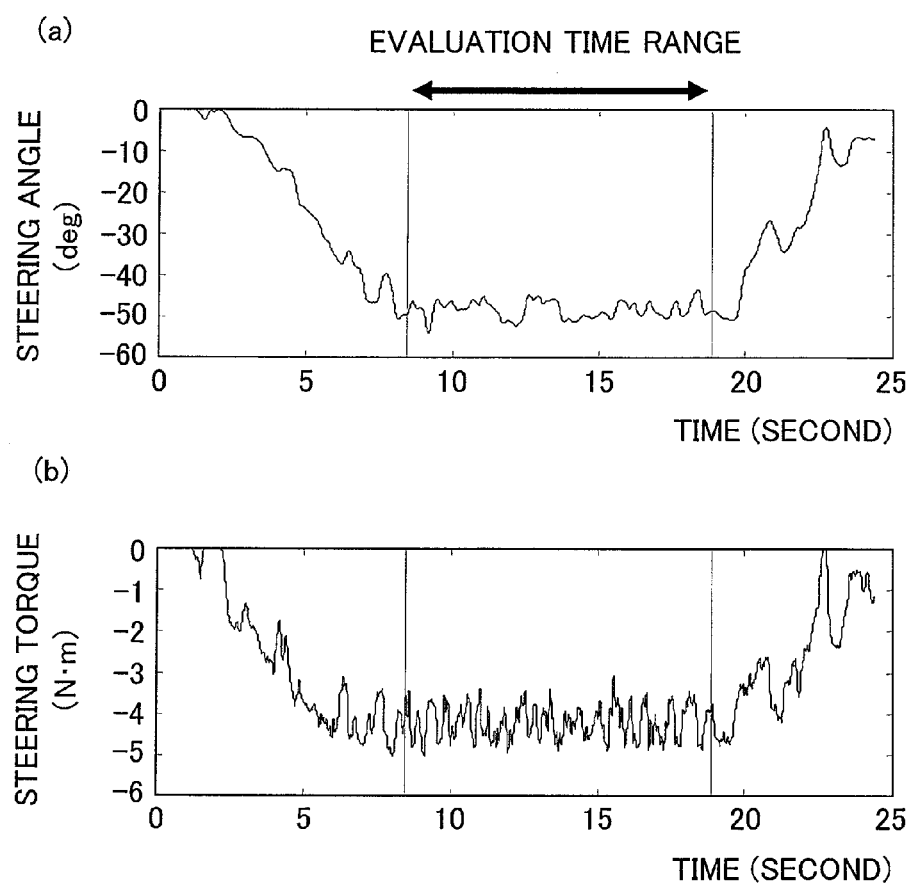
FIG. 6 Examples of time-series information detected by the method according to the present invention, in which (a) shows an example of time-series steering angle information, and (b) shows an example of time-series operation torque information.

It should be noted that the above-mentioned judgment (judgment as to whether vehicle 11 is traveling by following predetermined traveling conditions) may also be performed by using the detection result obtained by the second vehicle sensor 20. For example, in the case where the vehicle 11 is driven under the traveling condition shown in FIG. 4, (absolute values of) the steering angle and the steering torque gradually increase as the vehicle 11 turns its way from a straight path to a section having a constant curvature. Each of the absolute values then takes a substantially constant value in the section having a constant curvature, and gradually reduces to approach to zero (0) as the vehicle 11 again travels straightforward. FIG. 6(a) shows an example of a time-series steering angle detected in time series by the steering angle sensor 20a of the second vehicle sensor 20 when the vehicle 11 has been driven under the traveling condition shown in FIG. 4. Also, FIG. 6(b) is an example of a time-series steering torque detected by the steering torque sensor 20b of the second vehicle sensor 20 when the vehicle 11 has been driven under the traveling condition shown in FIG. 4. (The absolute values of) the steering angle and the steering torque fluctuate before and after the above-mentioned predetermined time range stored in advance, while the absolute values each take a substantially constant value in the section having a constant curvature. It may also be determined whether (absolute values of) the steering angle and the steering torque fluctuate before and after the above-mentioned predetermined time range and whether the absolute values each take a substantially constant value in the section having a constant curvature, to thereby judge whether the vehicle 11 is traveling at a predetermined traveling speed or not.

It should be noted that, in a case where the evaluation time range has not been set in advance, for example, information on the time-series steering angle or information on the time-series steering torque as shown in FIGS. 6(a) and (b) may be used for extracting/setting the evaluation target time range. As shown in FIGS. 6(a) and (b), the time-series steering angle or steering torque represents well enough the state of behavior of the vehicle. With reference to each of the information items shown in FIGS. 6(a) and (b), the time interval during which the value is kept substantially constant may be determined as being a time range during which the vehicle 11 is traveling a curved path having a constant curvature, and the time range thus determined may be set as the evaluation time range. Alternatively, the detection result obtained by the above-mentioned third vehicle sensor 22 may be used for determining a timing at which the vehicle 11 has turned its way to the curved path or a timing at which the vehicle 11 has passed through the curved path to travel a straight path again, and a time range defined by those timings may be set as the evaluation time range. Still alternatively, the time-series traveling trajectory of the vehicle 11 detected by the GPS sensor 15c may be used for extracting a time range during which the vehicle 11 is travelling a curved path having a constant curvature, and the time range thus extracted may be set as the evaluation time range.

As in each of the above-mentioned examples, in a case where, for example, the vehicle 11 is provided with various vehicle sensors in advance and the detection results obtained by those sensors can be used, the evaluation time range may be set and identified based on the detection results. However, according to the present invention, even in the case where the vehicle 11 is not provided with the vehicle sensors as described above, the traveling condition is set in advance and the vehicle 11 is driven under the set traveling condition, to thereby make it possible to correctly set, as the evaluation time range, a time range during which the vehicle 11 is cornering on a curved path having a constant curvature according to the operation of the driver 12. According to the present invention, for the purpose of reducing a ratio of needless noise components included in the myoelectric potential signal so as to determine drivability of the vehicle with higher accuracy as described above, the fluctuation reference value is calculated based on information on the myoelectric potential corresponding to the evaluation time range during which the vehicle is passing through a curved path having a constant curvature. However, how to set the evaluation time range is not specifically limited thereto.

The intensity reference value calculated by the calculating unit 46 indicates average magnitude of myoelectric potentials of a muscle involved in the operation. In other words, the intensity reference value corresponds to information indicating an average intensity of activity of a muscle involved in this operation, and more specifically, to information indicating an average intensity of the muscle. The intensity reference value may preferably be obtained as an arithmetic mean value or a root mean square (RMS) of the values of the above-mentioned smoothed waveform in a predetermined evaluation time range. The intensity reference value may also be an RMS value of a time-series myoelectric potential signal which is yet to be rectified and smoothed. In this embodiment, the intensity reference value indicates (an average magnitude of) a intensity of activity of the first muscle of the driver 12, the first muscle being necessary for the steering of the vehicle. The intensity reference value in this embodiment may also indicate a degree of magnitude of a load imposed on the driver 12 in relation to the steering operation of the vehicle 11 when the driver is steering the vehicle 11, that is, a level of steering force applied to the steering wheel of the vehicle 11. The greater intensity reference value related to the driver 12 means that the steering wheel of the vehicle 11 is heavy and the steering response thereof is relatively low while the driving stability thereof is relatively high. In contrast, the smaller intensity reference value means that the vehicle 11 can be lightly steered and has relatively high steering response, but the driving stability thereof is relatively low.

Meanwhile, the fluctuation reference value corresponds to information indicating a fluctuation amount of the myoelectric potentials of a muscle involved in the operation, the information indicating a scattering degree of the values of the myoelectric potential corresponding to the activity intensity. The fluctuation reference value may preferably be obtained as at least one of the standard deviation, the dispersion, the distribution range of the values of the smoothed waveform, and an RMS value of a waveform obtained by subjecting the time-series myoelectric potential signal to temporal differentiation in a predetermined evaluation time range. The fluctuation reference value indicates a level of steering adjustment (degrees of both of frequency and the magnitude thereof) made by the driver 12 when driving the vehicle 11 at a constant curvature. The greater fluctuation reference value related to the driver 12 indicates that the driver 12 is making steering adjustments at higher frequency and more greatly. When the above-mentioned fluctuation reference value related to the driver 12 is larger, it can be said that the vehicle 11 is relatively high in steering response while relatively low in stability. On the other hand, when the above-mentioned fluctuation reference value is smaller, it can be said that the vehicle 11 is relatively low in steering response while relatively high in stability.

Figure 5:
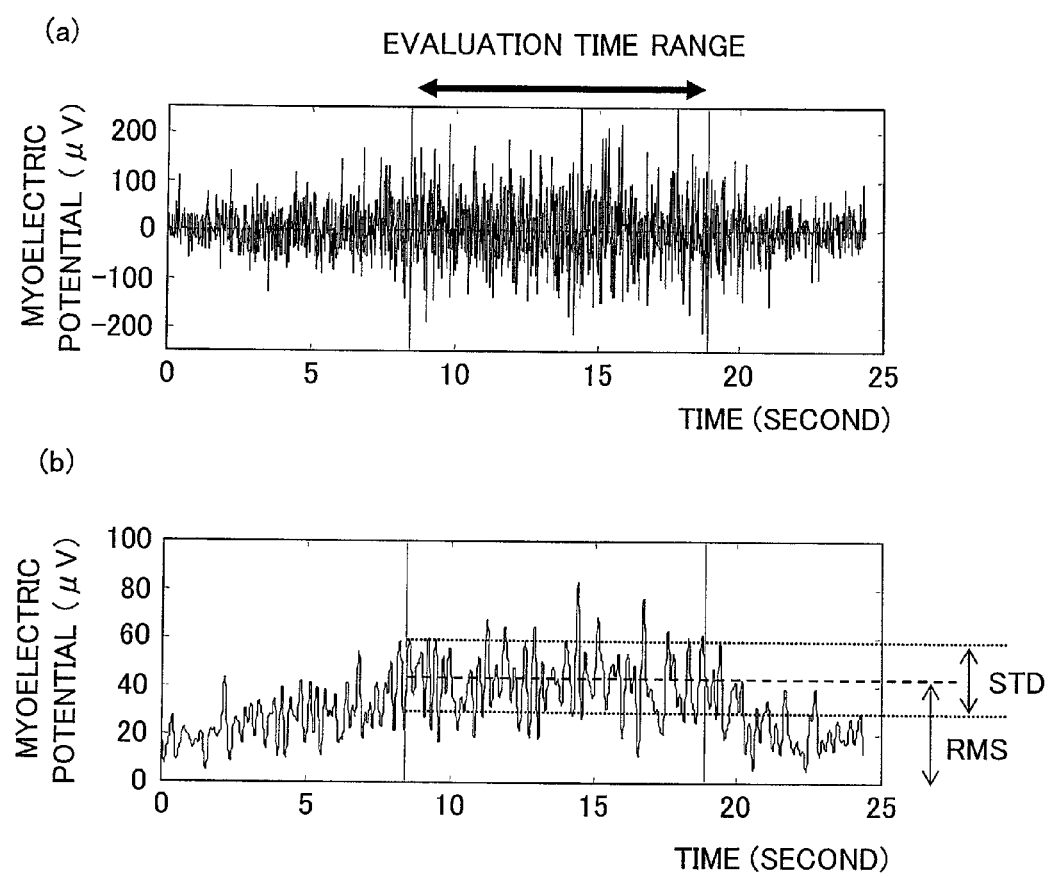
FIG. 5 (a) shows an example of a myoelectric potential signal acquired by the method according to the present invention, and (b) shows a time-series smoothed waveform of the myoelectric potential signal shown in (a).

FIG. 5(*b*) also shows magnitudes of the intensity reference value (RMS value in FIG. 5(*b*)) and the fluctuation reference value (standard deviation; STD in FIG. 5(*b*)), which have been obtained based on the smoothed waveform of the right deltoid muscle of the driver 12 corresponding to the above-mentioned evaluation time range.

Figure 7:
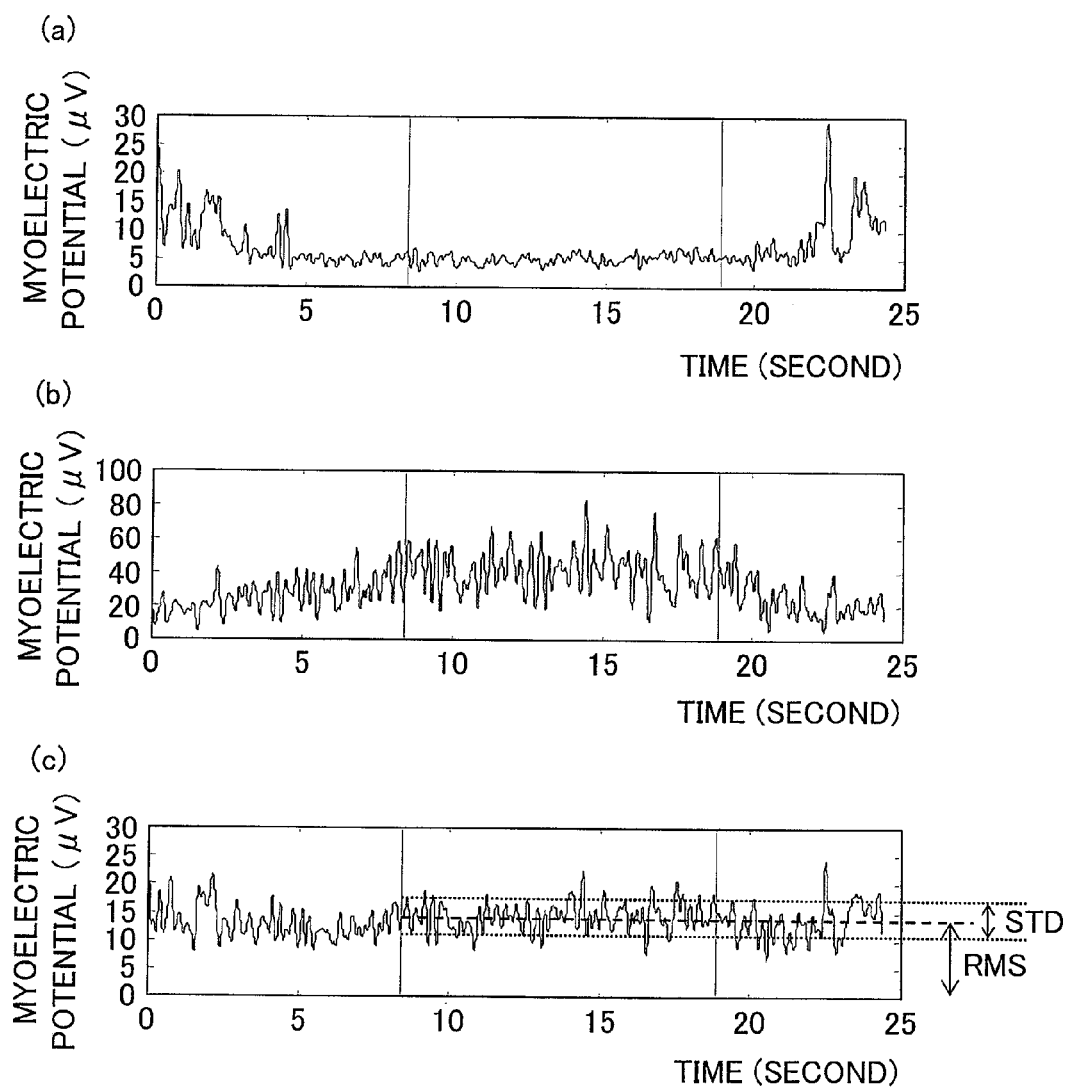
FIG. 7 (a) shows an example of a time-series myoelectric potential signal of a left deltoid muscle, which is acquired by the method of the present invention, (b) shows an example of a time-series myoelectric potential signal of a right deltoid muscle, which is acquired by the method of the present invention, and (c) shows an example of a time-series waveform of an intensity of a simultaneous activity of the right and left deltoid muscles of a driver.

It should be noted that the intensity reference value and the fluctuation reference value may be derived based on the myoelectric potentials of both of the right and left deltoid muscles. FIG. 7(*a*) shows the smoothed waveform obtained as described above with respect to the left deltoid muscle of the driver 12 when the vehicle 11 has been driven under the traveling conditions shown in FIG. 4. FIG. 7(*b*) shows a waveform similar to that of FIG. 5(*b*), which is a smoothed waveform obtained with respect to the right deltoid muscle of the driver 12. Further, FIG. 7(*c*) shows a waveform indicating the simultaneous activity intensity of the right and left deltoid muscles of the driver 12, which has been obtained based on the smoothed waveform of the left deltoid muscle shown in FIG. 7(*a*) and the smoothed waveform of the right deltoid muscle shown in FIG. 7(*b*). The simultaneous activity intensity in FIG. 7(*c*) is a geometric mean value per unit time of the values of the smoothed waveforms of the right and left deltoid muscles. FIG. 7(*c*) also shows magnitudes of the intensity reference value (RMS value in FIG. 7(*c*)) and the fluctuation reference value (standard deviation; STD in FIG. 7(*c*)), which have been obtained based on the simultaneous activity intensity waveform of the driver 12 corresponding to the above-mentioned evaluation time range. The intensity reference value and the fluctuation reference value both relate to the simultaneous activity intensity waveform. According to the present invention, the intensity reference value and the fluctuation reference value may be obtained respectively based on the myoelectric potentials of both of the right and left deltoid muscles as described above. For example, the simultaneous activity intensity waveform can be suitably adopted in a case of obtaining the intensity reference value and the fluctuation reference value with respect to a driver who positively activates both the right and left deltoid muscles while rotating the steering wheel in one direction. It should be noted that in a case of obtaining each value based on both the right and left deltoid muscles, the values may be obtained based on an arithmetic mean value per unit time of the values of the smoothed waveforms of both the right and left deltoid muscles. The type of the waveform indicating the simultaneous activity intensity of the first muscles on the right and left sides is not specifically limited. The intensity reference value and the fluctuation reference value calculated in the calculating unit 46 are output to the evaluating unit 48.

The evaluating unit 48 receives the values calculated in the calculating unit 46, and evaluates the drivability of the vehicle 11 based on both of the intensity reference value and the fluctuation reference value.

In general, a driver driving a vehicle uses the steering wheel not only for the driving operation but also to support the body of the driver. In other words, a driver driving a vehicle holds the steering handle, to thereby prevent the body of the driver from being displaced or changed in posture. Accordingly, in order to support a driver's body, it is preferable that the steering force applied to the steering wheel be heavier (in other words, it is preferable that the stability of the vehicle be higher). In addition, to make the steering wheel heavy produces an effect of causing the driver to slowly input the steering operation, which results in an effect of increasing the stability of the vehicle. However, the steering force applied to the steering wheel, when increased more than necessary, makes it difficult for the driver to input a steering operation as intended, with the result that the steering response of the vehicle is significantly deteriorated. Also, when the steering wheel is too heavy, a burden to be imposed on the driver is increased, which may cause the driver to feel fatigue or give the driver a sense of discomfort. On the other hand, when the steering wheel is light and can be steered by a significantly light force, the steering wheel cannot be used as mean for supporting the driver's body. In this case, the vehicle is easy to sway, which increases a frequency of steering adjustment. When the vehicle is high in driving stability, the vehicle is in a state where the vehicle can be steered by a minimum muscle force (steering wheel is lightly operated) while the frequency of steering adjustment is as low as possible. In other words, when the above-mentioned parameter value indicating frequency of steering adjustment and the intensity reference value indicating the level of the steering force applied to the steering wheel both have smaller values, the drivability of the vehicle is higher.

The evaluating unit 48 creates a scatter diagram which has, for example, both the intensity reference value and the fluctuation reference value on the coordinate axes thereof, in which points are plotted in combination of the intensity reference value and the fluctuation reference value. Then, the level of the drivability is evaluated based on the position of the point of combination in the scatter diagram. As described above, when the intensity reference value and the fluctuation reference value have smaller values, the drivability of the vehicle is higher. For example, in the above-mentioned scatter diagram, it can be determined that the drivability of the vehicle is higher when the position of the point of the combination is plotted in a region closer to the origin point. Alternatively, the score corresponding to the intensity reference value and the score corresponding to the fluctuation reference value are summed, and it may be determined that the drivability of the vehicle is higher when the sum of the scores is smaller. The determination result of the evaluating unit 48 is output to be displayed on the display 52. Further, in a case of performing comparative evaluations relatively on a plurality of vehicles of different specifications, the evaluating unit 48 may create a graph for comparing the values (intensity reference value and fluctuation reference value) for the respective specifications, and the graph may be output to be displayed on the display 52.

Figure 8:
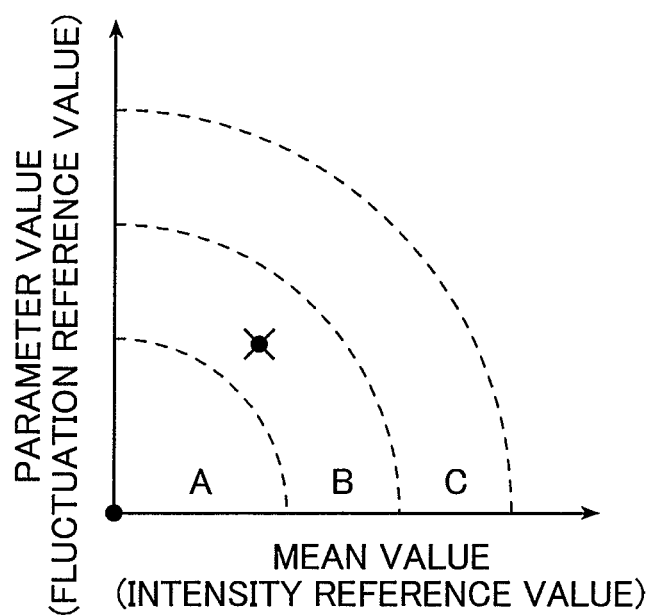
FIG. 8 An example of a scatter diagram created by an evaluating unit of the apparatus according to the present invention.

FIG. 8 shows an example of the scatter diagram created by the evaluating unit 48. The evaluating unit 48 creates a scatter diagram as shown in FIG. 8 which has both the intensity reference value and the fluctuation reference value on the coordinate axes thereof, in which a point of combination of the intensity reference value and the fluctuation reference value is plotted. For example, in the scatter diagram as described above, when the point of combination is plotted in a region A, the drivability may be determined as being high; when the point of combination is plotted in a region B, the drivability may be determined as being ordinary; and when the point of combination is plotted in a region C, the drivability may be determined as being low. In the example shown in FIG. 8, the evaluating unit 48 determines the drivability as being ordinary, and outputs the evaluation result to be displayed on the display 52.

Figure 9:
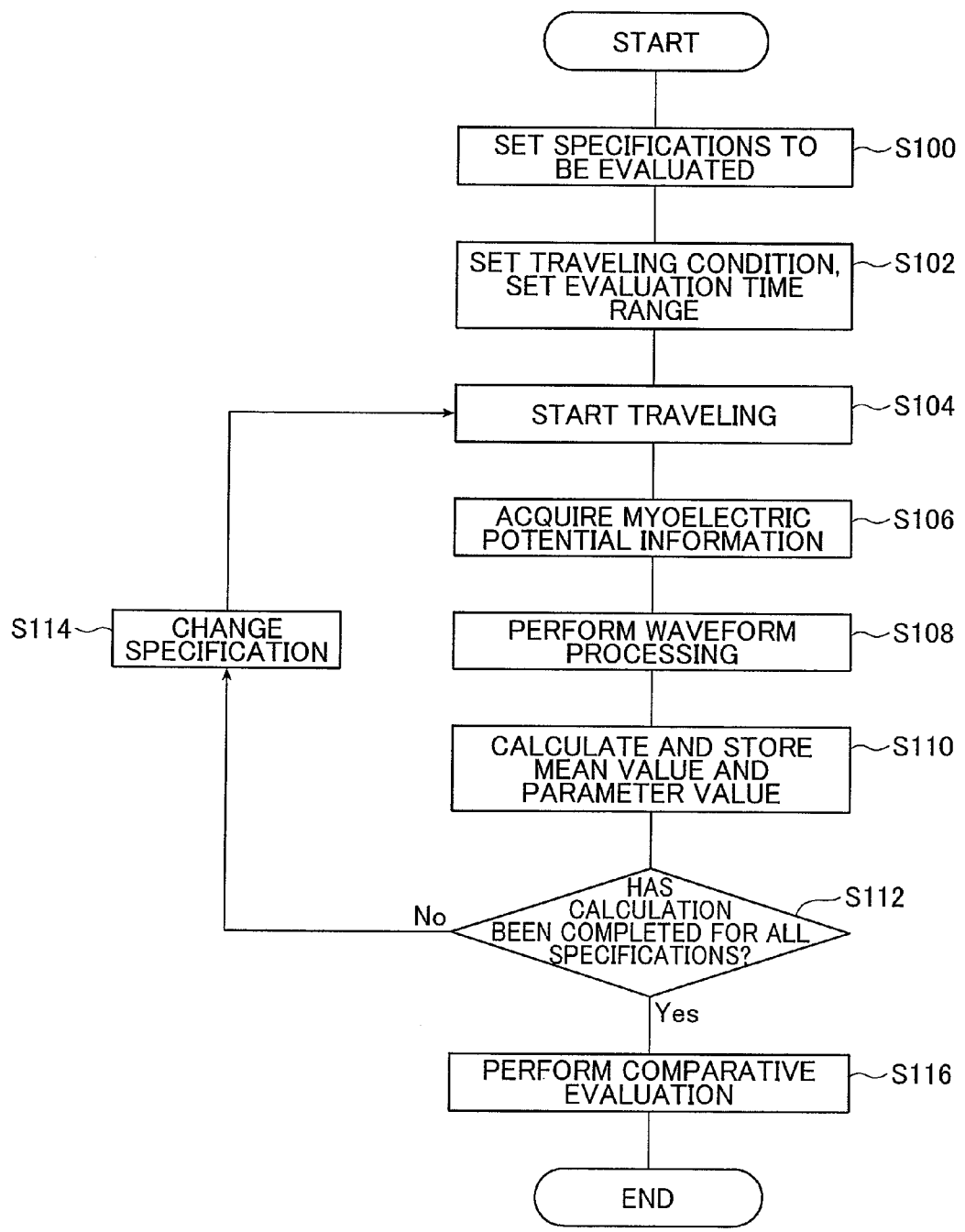
FIG. 9 A flowchart illustrating an example of the method according to the present invention.

FIG. 9 is a flowchart of an example of the method of the present invention, which is performed by using the evaluating apparatus 10. In the following, a description will be given of an embodiment where the drivability is evaluated with respect to each of a plurality of (three) vehicles of different specifications. According to the vehicle specifications $C_1$ to $C_3$ in the following embodiment, the specifications have the same vehicle except tire types provided thereto. Specifically, one of a plurality of tires $T_1$ to $T_3$ of different specifications is provided for each specification. First, specifications to be evaluated are set (Step S100). According to this embodiment, the vehicles $C_1$ to $C_3$ of different specifications (each corresponding to vehicle 11) are each driven by one of five drivers $P_1$ to $P_5$ (each corresponding to driver 12), and the drivability of each of the vehicles $C_1$ to $C_3$ is evaluated based on the activity intensity of the first muscle of each of the drivers during the driving operation. In Step S100, specifications of combination of each of the drivers and each of the vehicles (in this embodiment, 5×3=15 specifications) are set.

Next, a traveling condition is set for performing comparative evaluations on the vehicle drivability with respect to the specifications, while the above-mentioned evaluation time range is set for deriving the above-mentioned values (intensity reference value and fluctuation reference value) (Step S102). In this case, the traveling condition is common to all the specifications under which the vehicle 11 is driven. In this embodiment, the traveling condition shown in FIG. 4 is set. Then, the time range corresponding to the bold line in FIG. 4 is set as the evaluation time range, during which the vehicle is passing through a curved path having a constant curvature. The condition of the traveling path on which the vehicle 11 is to travel and the condition of the traveling speed are predetermined, and therefore the time range during which the vehicle is traveling at a constant curvature is already identified with respect to the time at which the vehicle 11 has started traveling. Information on the evaluation time range defined as described above is input by an operator by using an input means, which is not shown, connected to the data processing unit 40, and stored in the memory 43.

After the setting is completed, driving of the vehicle is started under one of the specifications (for example, combination of vehicle $C_1$ and driver $P_1$) (Step S104). During the driving of the vehicle, the acquiring unit 42 acquires information on the myoelectric potential detected by the detection sensor 34 (Step S106). According to the traveling condition of FIG. 4, the vehicle corners a curved path having a constant curvature to the left, and in this embodiment, the myoelectric potential signal of the deltoid muscle on the outer side with respect to the cornering direction (that is, right deltoid muscle) is obtained for each specification. The time-series myoelectric potential signal acquired by the acquiring unit 42 is transmitted to the processing unit 44. The processing unit 44 samples the received time-series myoelectric potential signal to subject the signal to full-wave rectification, and then smoothes the signal by using a smoothing filter (low-pass filter), to thereby create a signal waveform (smoothed waveform) of the myoelectric potential for at least one of the right and left deltoid muscles (Step S108).

Next, the calculating unit 46 obtains the above-mentioned intensity reference value and the above-mentioned fluctuation reference value based on the smoothed waveform, and stores the obtained values in the memory 43 (Step S110). At this time, the information on the evaluation time range stored in the memory 43 is read out, and the values are obtained by using the information on the smoothed waveform in the evaluation time range. In this embodiment, as the intensity reference value, for example, a root mean square (RMS) value of the values of the smoothed waveform in the evaluation time range is obtained. Also, as the fluctuation reference value, for example, a value of the standard deviation (STD) of the values of the smoothed waveform in a predetermined evaluation time range is obtained.

Next, it is determined whether the calculation and storage of the intensity reference value and the fluctuation reference value have been completed for all the specifications set in Step S100 (Step S112). In a case where there still remains any specification for which the intensity reference value and the fluctuation reference value have not been calculated and stored, that is, in a case where the determination result in Step S112 is "No", the specification to be evaluated is changed (Step S114), and the processes of Steps S104 to S112 are repeated. Those processes are repeatedly performed until the intensity reference value and the fluctuation reference value are calculated/stored for all the specifications to be evaluated (all the 15 specifications in this embodiment), that is, until the determination result in Step S112 turns to "Yes".

When the calculation/storage of the intensity reference value and the fluctuation reference value for all the specifications has been completed, the evaluating unit 48 performs comparative evaluation of the drivability with respect to the respective specifications (S116). The evaluating unit 48 creates a graph or a scatter diagram for performing comparative evaluation of the drivability with respect to the respective specifications.

Figure 10:
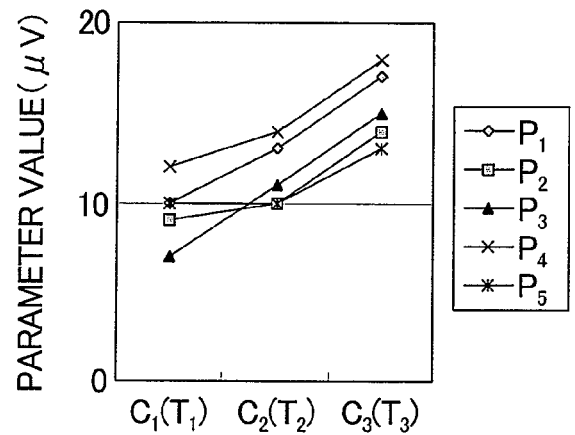
FIG. 10 (a) is a graph illustrating parameter values obtained by the method of the present invention, in which the parameter values are categorized in terms of respective specifications of different vehicles, (b) is a graph illustrating values shown in (a), which are normalized for each driver, and (c) illustrates arithmetic mean values and a distribution thereof based on the graph after normalization shown in (b).
Figure 10:
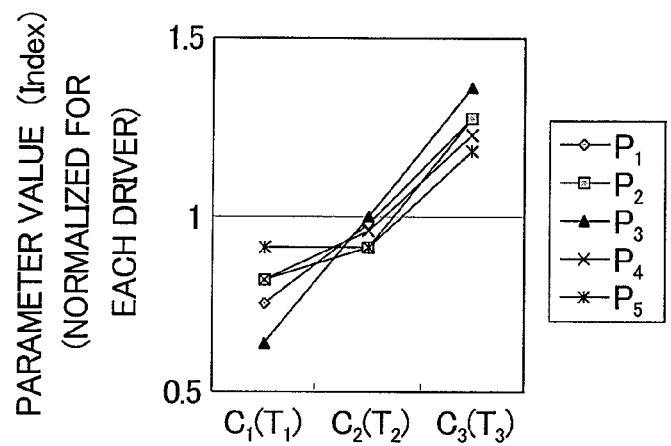
Figure 10:
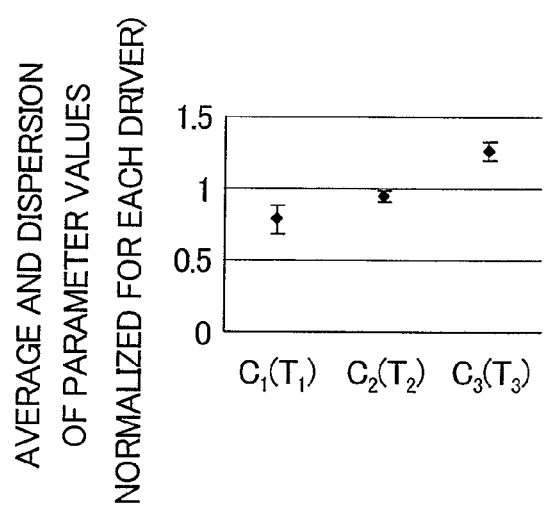

FIG. 10(*a*) is a graph illustrating the fluctuation reference values calculated for the specifications, in which the fluctuation reference values are categorized in terms of the vehicles $C_1$ to $C_3$ (each being provided with one of tires $T_1$ to $T_3$ of different specifications). FIG. 10(*b*) shows values of indexes (Index) each being normalized for the respective drivers $P_1$ to $P_5$ such that the fluctuation reference values obtained in the cases where the drivers $P_1$ to $P_5$ have performed driving operation of the vehicles $C_1$ to $C_3$ have a mean value of 1. The index values are categorized for the respective vehicles $C_1$ to $C_3$. As shown in FIG. 10(*b*), when the parameter value is normalized for each of the plurality of drivers, it is possible to eliminate an influence on the activity amount of the muscle in the steering operation due to the difference of the driving manners of the individual drivers, which makes it possible to quantitatively perform comparative evaluation on the drivability of each of the vehicles with accuracy. Further, FIG. 10(*c*) shows a result obtained by determining an arithmetic mean value and a dispersion of the fluctuation reference value categorized in terms of each of the vehicles $C_1$ to $C_3$ and normalized for each of the drivers shown in FIG. 10(b). It should be noted that, according to the present invention, normalization based on Z score may further be performed, with respect to the evaluation result, for each of the drivers. Specifically, normalization may be performed such that the mean value of 0 (zero) and the variance of 1 can be obtained for each of the drivers. The normalization based on Z score is effective, when the normalization has been performed as described above such that the mean value of 1 can be obtained, for example, in a case where the difference among the individual drivers in terms of the dispersion range of the fluctuation reference value is relatively large. In other words, when the normalization based on Z score is performed, it is possible to eliminate the influence on the activity amount of the muscle in the steering operation due to the variation of the respective drivers.

As can be determined based on each of the graphs shown in FIGS. 10(a) to 10(c), the fluctuation reference value is smallest in the vehicle specification $C_1$ provided with the tire $T_1$. Among the vehicles $C_1$ to $C_3$ which are different from one another, it can be identified that the vehicle $C_1$ has a smallest amount of the adjustment steering and is highest in stability when traveling under the set traveling conditions. Also, the vehicle specification $C_3$ provided with the tire $T_3$ is highest in fluctuation reference value. Among the vehicles $C_1$ to $C_3$ which are different from one another, it can be identified that the vehicle $C_3$ is lowest in stability.

Figure 11:
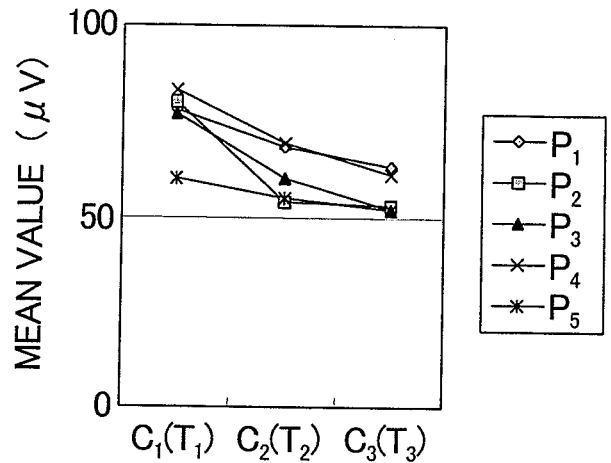
FIG. 11 (a) is a graph illustrating mean values obtained by the method of the present invention, in which the mean values are categorized in terms of respective specifications of different vehicles, (b) is a graph illustrating values shown (a), which are normalized for each driver, and (c) illustrates arithmetic mean values and a distribution thereof based on the graph after normalization shown in (b).
Figure 11:
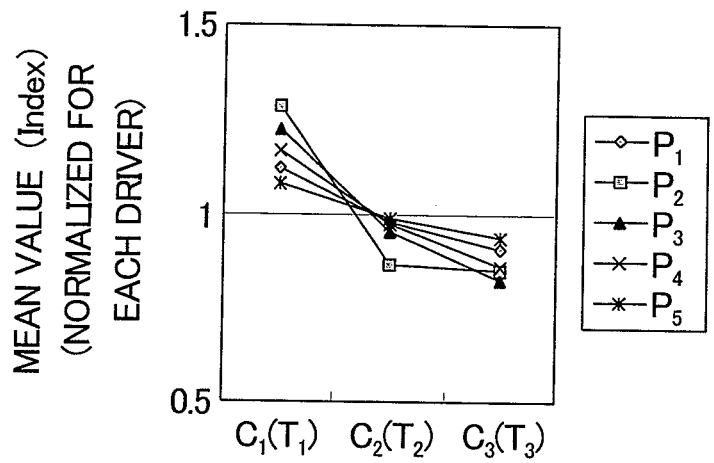
Figure 11:
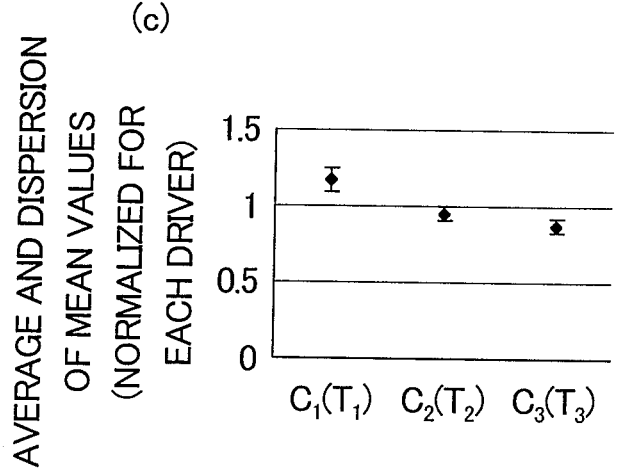

FIG. 11(a) is a graph illustrating the above-mentioned intensity reference values for the respective specifications, in which the intensity reference values are categorized in terms of the vehicles $C_1$ to $C_3$ (each being provided with one of the tires $T_1$ to $T_3$ of different specifications). FIG. 11(b) shows values of indexes (Index) each being normalized for the respective drivers $P_1$ to $P_5$ such that the intensity reference values obtained in the cases where the drivers $P_1$ to $P_5$ have performed driving operation of the vehicles $C_1$ to $C_3$ have a mean value of 1. The values of indexes are categorized for the respective vehicles $C_1$ to $C_3$. Further, FIG. 11(c) shows a result obtained by determining an arithmetic mean value and a dispersion of the intensity reference value which are categorized in terms of each of the vehicles $C_1$ to $C_3$ and normalized for each of the drivers shown in FIG. 11(b).

As can be determined based on each of the graphs shown in FIGS. 11(a) to 11(c), the intensity reference value is largest in the vehicle specification $C_1$ provided with the tire $T_1$. Among the vehicles $C_1$ to $C_3$ which are different from one another, it can be identified that the vehicle $C_1$ is largest in steering force applied to the steering wheel and lowest in responsiveness. Also, the intensity reference value is smallest in the vehicle specification $C_3$ provided with the tire $T_3$. Among the vehicles $C_1$ to $C_3$ which are different from one another, it can be identified that the vehicle $C_3$ is lightest in steering force applied to the steering wheel and highest in responsiveness.

Figure 12:
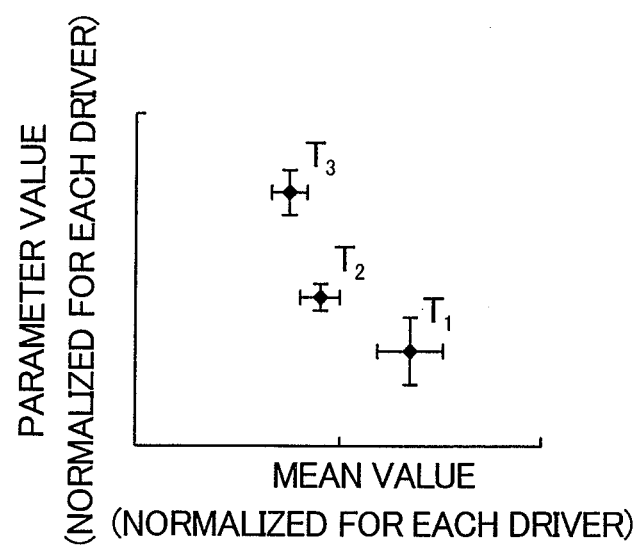
FIG. 12 A scatter diagram in which relations between the average value of the parameters shown in FIG. 10(c) and the average value of the mean values shown in FIG. 11(c) are plotted on orthogonal coordinates.

FIG. 12 is a scatter diagram in which the relations between the average value of the fluctuation reference values shown in FIG. 10(c) and the average value of the intensity reference values shown in FIG. 11(c) are plotted on orthogonal coordinates. FIG. 12 also shows a dispersion of the parameters (normalized values). As described above, when the parameter value indicating the degree of steering adjustment and the intensity reference value indicating the level of the steering force applied to the steering wheel both have smaller values, the drivability of the vehicle is higher.

In the scatter diagram as described above, it can be determined that the drivability of the vehicle is higher when the position of the combination is plotted in a region closer to the origin point. According to the example shown in FIG. 12, it can be determined that the vehicle $C_2$ provided with the tire $T_2$ is highest in drivability. In Step S116, the scatter diagram as described above is output to be displayed on the display 52 and the determination result indicating that the vehicle $C_2$ provided with the tire $T_2$ is highest in drivability is also output to be displayed. The method of evaluating the drivability of a vehicle according to the present invention can be implemented as described above.

It should be noted that the inventor(s) of the present invention has performed an experiment in order to verify the effect of the present invention. In the following, the result of the experiment will be described. In the verification experiment, a subjective evaluation was made for each of the specifications (15 specifications different from one another) in the above-mentioned embodiment by each of the drivers $P_1$ to $P_5$ driving a vehicle. In other words, the five different drivers $P_1$ to $P_5$ each made a quantitative evaluation based on the sense of the driver, in each of the cases of steering the vehicles $C_1$ to $C_3$. Specifically, each of the drivers gave a score (grade) of one of 0 to 7 to each of the vehicles the driver had driven, in terms of "line trace performance" and "steering force applied to the steering wheel" when the driver had driven the vehicle. As regards the "line trace performance", a score of 3 was set as a standard, and the vehicle was graded with a score closer to 0 (lower score) when the driver felt that the vehicle was poorer in line trace performance, while the vehicle was graded with a score closer to 7 (higher score) when the driver felt that the vehicle was better in line trace performance. As regards the "steering force applied to the steering wheel", a score of 3 was set as a standard, and the vehicle was graded with a score closer to 0 (lower score) when the driver felt that the force applied to the steering wheel of the vehicle was heavier, while the vehicle was graded with a score closer to 7 (higher score) when the driver felt that the steering wheel of the vehicle was light. In this case, the "line trace performance" refers to a sense corresponding to the responsiveness of a vehicle, and the "steering force applied to the steering wheel" refers to a sense corresponding to the stability of a vehicle.

Figure 13:
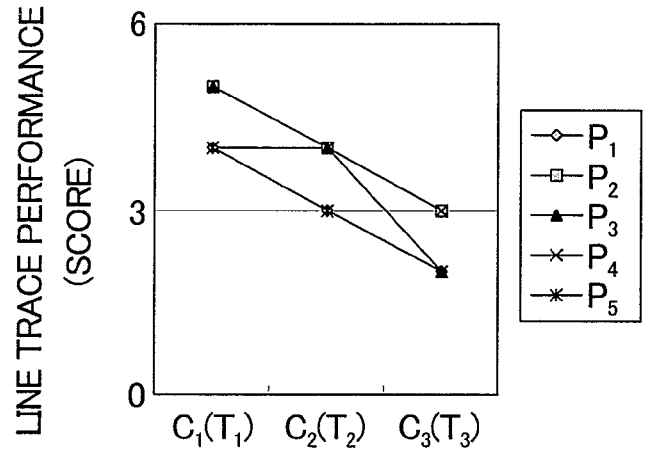
FIG. 13 (a) is a graph illustrating a result of a verification experiment performed by the inventor(s) of the present invention, which shows subjective evaluation score values on "line trace performance", the values being categorized in terms of respective specifications of different vehicles, (b) is a graph illustrating the values shown in FIG. 13(a), which are normalized for each driver, and (c) is a scatter diagram illustrating a correspondence between the result of the verification experiment shown in (b) and the parameter values shown in FIG. 10(c).
Figure 13:
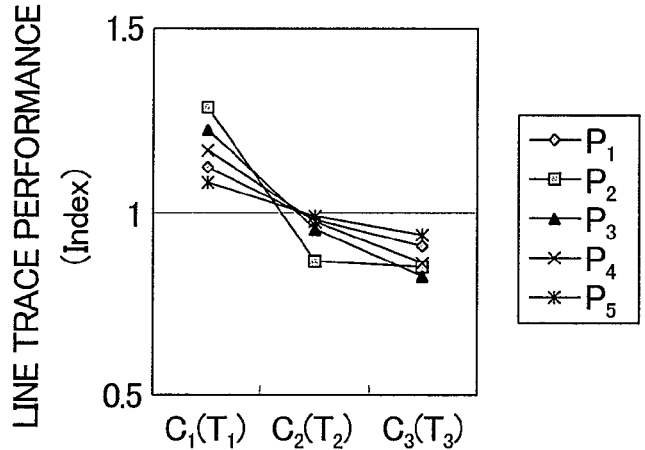
Figure 13:
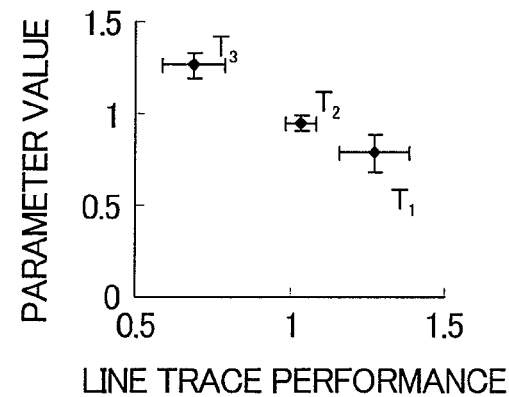

FIG. 13(a) is a graph showing the score values in relation to the "line trace performance" for the respective specifications, in which the score values are categorized in terms of the vehicles $C_1$ to $C_3$ (each being provided with one of tires $T_1$ to $T_3$ of different specifications). FIG. 13(b) shows values of indexes (Index) each being normalized for the respective drivers $P_1$ to $P_5$ such that the scores for the "line trace performance" in the cases where the drivers $P_1$ to $P_5$ have performed driving operation of the vehicles $C_1$ to $C_3$ have a mean value of 1. The index values are categorized for the respective vehicles $C_1$ to $C_3$. Also, FIG. 13(c) is a scatter diagram in which the correspondence between the result of obtaining an average and a dispersion of the index values shown in FIG. 13(b) for each of the vehicles and the average and the dispersion of the fluctuation reference values of the respective vehicles shown in FIG. 10(c). As can be determined by comparing FIGS. 10(a) and 10(b) with FIGS. 13(a) and 13(b), when the fluctuation reference value is smaller, the score of the "line trace performance" is higher (that is, responsiveness of vehicle is higher), while the fluctuation reference value is larger, the score of the "line trace performance" is lower (that is, responsiveness of vehicle is lower). As shown in FIG. 13(c), there is exhibited a satisfactory linear relation between the result of the sensory evaluation as described above and the fluctuation reference value. The fluctuation reference value used in the present invention quantitatively represents the responsiveness of a vehicle with accuracy.

Figure 14:
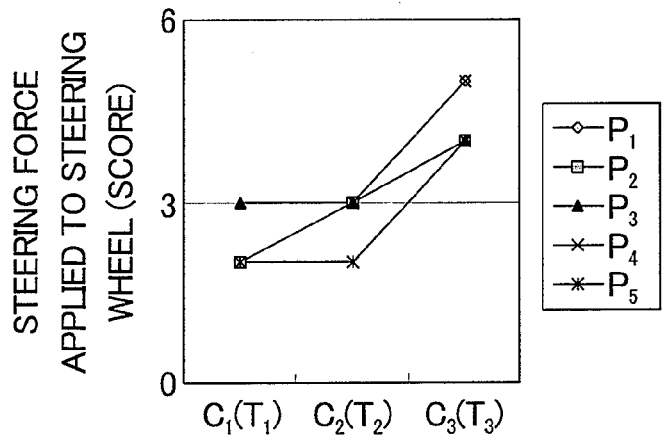
FIG. 14 (a) is a graph illustrating the result of the verification experiment performed by the inventor(s) of the present invention, which shows subjective evaluation score values on "steering force applied to a steering wheel", the values being categorized in terms of respective specifications of different vehicles, (b) is a graph illustrating the values shown in (a), which are normalized for each driver, and (c) is a scatter diagram illustrating a correspondence between the result of the verification experiment shown in (b) and the parameter values shown in FIG. 10(c).
Figure 14:
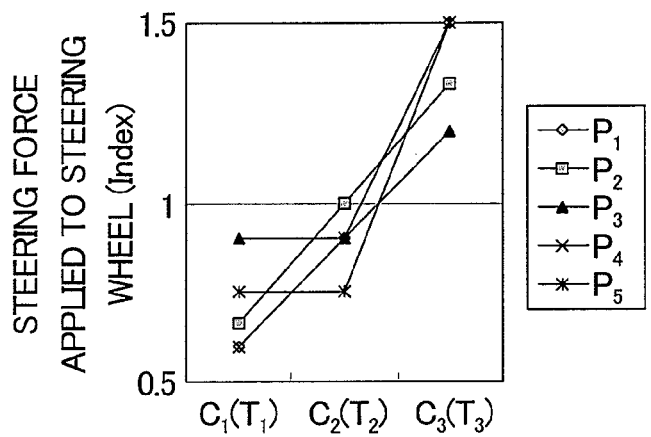
Figure 14:
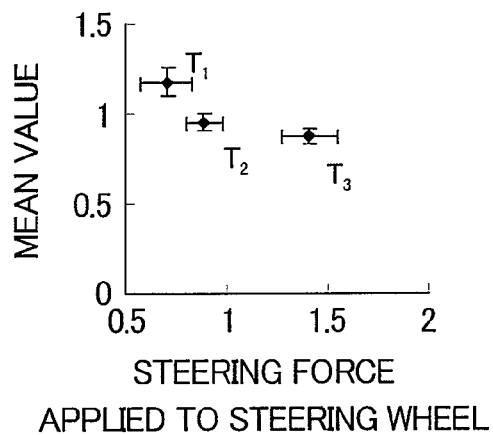

Further, FIG. 14(a) is a graph showing the score values in relation to the "steering force applied to the steering wheel" for the respective specifications, in which the score values are categorized in terms of the vehicles $C_1$ to $C_3$ (each being provided with one of tires $T_1$ to $T_3$ of different specifications). FIG. 14(b) shows values of indexes (Index) each being normalized for the respective drivers $P_1$ to $P_5$ such that the scores for the "steering force applied to the steering wheel" in the cases where the drivers. $P_1$ to $P_5$ have performed driving operation of the vehicles $C_1$ to $C_3$ have a mean value of 1. The index values are categorized for the respective vehicles $C_1$ to $C_3$. Also, FIG. 14(c) is a scatter diagram in which the correspondence between the result of obtaining an average and a dispersion of the index values shown in FIG. 14(b) for each of the vehicles and the average and the distribution of the intensity reference values of the respective vehicles shown in FIG. 11(c) for each of the vehicles. As can be determined by comparing FIGS. 11(a) and 11(b) with FIGS. 14(a) and 14(b), when the above-mentioned intensity reference value is smaller, the score of the "steering force applied to the steering wheel" is higher (that is, steering wheel is lighter and stability of vehicle is smaller), and when the intensity reference value is larger, the score of the "steering force applied to the steering wheel" is smaller (that is, force applied to the steering wheel is heavier and stability of vehicle is larger). As shown in FIG. 14(c), there is exhibited a satisfactory linear relation between the result of the subjective evaluation as described above and the above-mentioned intensity reference value. As described above, it has been confirmed that the intensity reference value used in the present invention quantitatively represents the stability of a vehicle with accuracy.

It should be noted that, according to the present invention, in order to specifically make an evaluation only with regard to the responsiveness of a vehicle, the above-mentioned fluctuation reference value may be solely calculated and the responsiveness of the vehicle may be evaluated, as the drivability of the vehicle, based merely on the fluctuation reference value. However, when the fluctuation reference value quantitatively representing the responsiveness of a vehicle with accuracy is used together with the intensity reference value quantitatively representing the stability of a vehicle with accuracy, it is possible to quantitatively evaluate the drivability of a vehicle with accuracy, the drivability being decisively determined based on the balance between both the responsiveness of the vehicle and the stability of the vehicle. According to the method of evaluating the drivability of a vehicle of the present invention, it is preferable to calculate both the above-mentioned fluctuation reference value and the intensity reference value, and both of those values may preferably used for evaluating the drivability of the vehicle.

Further, in the above-mentioned example, the vehicle drivability is evaluated based on the time-series myoelectric potential signal of the first muscle (deltoid muscle in the above-mentioned embodiment) for operating a steering unit such as steering among muscles relating to the operation work of driving. However, according to the present invention, when driving the vehicle, the myoelectric potential signal for evaluating the drivability of a vehicle is not limited to the information on the myoelectric potential of the first muscle described above. As described above, the steering wheel also serves as a means for supporting the body of the driver, and accordingly, in a case where, for example, the steering wheel can be steered by a significantly light force, the steering wheel cannot be used as a means for supporting the body of the driver. In this case, the second muscle acts positively as the driver tries keeping the posture. The second muscle relates to the maintenance of the posture of the driver driving the vehicle, and examples of the second muscle include a trapezius muscle, a latissimus dorsi muscle, a levator scapulae muscle, a rhomboideus muscle, an erector spinae muscle, a fascia thoracolumbalis, which are located at the back of the driver and also include a sternocleidomastoid muscle located at the cervical region of the driver. According to the method of the present invention, the drivability of a vehicle may be evaluated based on the time-series myoelectric potential signal of the second muscle as described above. In other words, the fluctuation reference value and the intensity reference value may be obtained based on the time-series myoelectric potential signals of those second muscles, and those values may be used for evaluating the drivability of the vehicle. Alternatively, those values may also be used for evaluating, not only the drivability of the vehicle, but also for evaluating the holding capability of the seat or the degree of comfort of the seat.

Also, similarly to the above, the drivability of a vehicle may be evaluated based on the time-series myoelectric potential signal of the third muscle of a driver, which relates to the grip (holding) of the steering wheel of the driver. Examples of the third muscle include an extensor carpi radialis muscle, a common digital extensor muscle, a brachioradial muscle, and an extensor carpi ulnaris muscle, which are extensors/antagonists located in the front arm of the driver, and also include a flexor carpi radialis muscle, a flexor carpi ulnaris muscle, and a long palmar muscle, which are flexors/agonists located in the front arm of the driver. In other words, the above-mentioned fluctuation reference value and intensity reference value may be obtained based on the time-series myoelectric potential signal of the third muscle of the driver, and those values may be used for evaluating the drivability of the vehicle.

Also, in order to make an evaluation on the drivability of the vehicle in consideration of the speed controllability of the vehicle, the time-series myoelectric potential signal of the fourth muscle for operating a speed controlling unit of the driver may be used for evaluating the vehicle drivability. The fourth muscle includes, for example, a muscle used for controlling an operation of an accelerator pedal or a brake pedal of the vehicle. Examples of the fourth muscle include an extensor digitorum longus muscle and an anterior tibial muscle, which are antagonists located in an anterior group of the lower thigh of the driver, and also include a calf muscle and a soleus muscle, which are agonists located in a posterior group of the lower thigh of the driver. In other words, the above-mentioned fluctuation reference value and intensity reference value are obtained based on the time-series myoelectric potential signal of the fourth muscle of the driver, and those values may be used for evaluating the drivability of the vehicle.

The drivability of a vehicle can be determined as being high in the case where the driver is required to perform unnecessary operation as little as possible when the vehicle is traveling straightforward or traveling on a curved path having a constant curvature. In the case where the above-mentioned fluctuation reference value and the above-mentioned intensity reference value of the time-series myoelectric potential signal during driving of a vehicle are relatively small, the fluctuation reference value and the intensity reference value being obtained for each of the muscles such as the second muscle, the third muscle, or the fourth muscles as described above, the driver is not exerting an unnecessary force involved in the operation of the vehicle, and therefore the fluctuation of the force related to the operation is reduced. It can be said that the vehicle drivability can be evaluated from various views by using the muscle such as the second muscle, the third muscle, or the fourth muscle.

In the above, the method, the apparatus, and the program of the present invention have been described in detail. However, the present invention is not limited to the above-mentioned embodiment, and can be subjected to various modifications and alterations without departing from the gist of the present invention.

The invention claimed is:

1. A method of evaluating drivability of a vehicle using an apparatus comprising an acquiring unit, a calculating unit and an evaluating unit, comprising the steps of:
    acquiring by the acquiring unit a time-series myoelectric potential signal of only a muscle of a driver when the driver is performing a driving operation on the vehicle, the muscle being one of muscles for operating a steering means;
    obtaining by the calculating unit, based on the acquired time-series myoelectric potential signal, a parameter value representing a fluctuation amount of the time-series myoelectric potential signal and a mean value of the time-series myoelectric potential signal; and
    evaluating by the evaluating unit, based on both the parameter value and the mean value, the vehicle such that when the parameter value has a smaller value and the mean value has a smaller value, the drivability of the vehicle is higher,
    wherein:
    in obtaining the parameter value, the parameter value is obtained by the calculating unit by using a myoelectric potential signal corresponding to a time during which the vehicle is traveling under a predetermined traveling condition;
    the predetermined traveling condition comprises a condition that the vehicle travels on a traveling path which at least includes a curved path having a constant curvature;
    the traveling path is a path that the vehicle traveled on a straight path, gradually increases a steering angle so as to enter the curved path having the constant curvature, passes through the curved path having the constant curvature, and gradually increases the steering angle so as to again enter on the straight path;
    the parameter value indicates a level of both of frequency and magnitude of steering adjustment made by the driver when driving the vehicle under a predetermined traveling condition;
    the parameter value comprises at least one of a standard deviation, a dispersion, a distribution range of the time-series myoelectric potential signal, and a root mean square of the waveform obtained by subjecting the information corresponding to the time-series myoelectric potential signal to time differentiation; and
    the greater parameter value indicates that the driver is making steering adjustments at higher frequency and more greatly.

2. The method of evaluating drivability of a vehicle according to claim 1, wherein:
    the time-series myoelectric potential signal corresponds to information on a surface myoelectric potential of the muscle;
    the apparatus further comprising a processing unit;
    the method further comprising the step of rectifying and smoothing the information on the surface myoelectric potential by the processing unit; and
    in obtaining the parameter value, the parameter value is obtained based on a waveform obtained by rectifying and smoothing the information on the surface myoelectric potential by the calculating unit.

3. The method of evaluating drivability of a vehicle according to claim 1, wherein:
    in obtaining the parameter value, the parameter value is obtained by the calculating unit by using a myoelectric potential signal corresponding to a time during which the vehicle is traveling under a predetermined traveling condition; and
    the predetermined traveling condition is a condition that the vehicle travels on a curved path having a constant curvature.

4. The method of evaluating drivability of a vehicle according to claim 1, wherein:
    in obtaining the parameter value, the parameter value and the mean value are obtained by the calculating unit by using a myoelectric potential signal corresponding to a time during which the vehicle is traveling under a predetermined traveling condition; and
    the predetermined traveling condition is a condition that the vehicle travels on a traveling path which at least includes a curved path having a constant curvature.

5. The method of evaluating drivability of a vehicle according to claim 1, wherein:
    in obtaining the parameter value, the parameter value and the mean value are obtained by the calculating unit by using a myoelectric potential signal corresponding to a time during which the vehicle is traveling under a predetermined traveling condition; and
    the predetermined traveling condition comprises a condition that the vehicle travels on a curved path having a constant curvature.

6. The method of evaluating drivability of a vehicle according to claim 1, wherein the predetermined traveling condition further comprises a condition that the vehicle travels at a constant traveling speed.

7. An apparatus for evaluating drivability of a vehicle, comprising:
    an acquiring unit for acquiring a time-series myoelectric potential signal of only a muscle of a driver when the driver is performing a driving operation on the vehicle, the muscle being one of muscles for operating a steering means;
    a calculating unit for obtaining, based on the acquired time-series myoelectric potential signal, a parameter value representing a fluctuation amount of the time-series myoelectric potential signal and a mean value of the time-series myoelectric potential signal; and
    an evaluating unit for evaluating, based on both the parameter value and the mean value, the vehicle such that when the parameter value has a smaller value and the mean value has a smaller value, the drivability of the vehicle is higher,
    wherein, in obtaining the parameter value, the parameter value is obtained by the calculating unit by using a myoelectric potential signal corresponding to a time during which the vehicle is traveling under a predetermined traveling condition,
    the predetermined traveling condition comprises a condition that the vehicle travels on a traveling path which at least includes a curved path having a constant curvature, and the traveling path is a path that the vehicle traveled on a straight path, gradually increases a steering angle so as to enter the curved path having the constant curvature, passes through the curved path having the constant curvature, and gradually increases the steering angle so as to again enter on the straight path, wherein the parameter value indicates a level of both of frequency and magnitude of steering adjustment made by the driver when driving the vehicle under a predetermined traveling condition, the parameter value comprises at least one of a standard deviation, a dispersion, a distribution range of the time-series myoelectric potential signal, and a root mean square of the waveform obtained by subjecting the information corresponding to the time-series myoelectric potential signal to time differentiation, and the greater parameter value indicates that the driver is making steering adjustments at higher frequency and more greatly.

8. A non-transitory computer readable medium embodied with a program executed in an apparatus for evaluating drivability of a vehicle, the program causing a computer to execute the steps of:

acquiring a time-series myoelectric potential signal of only a muscle of a driver when the driver is performing a driving operation on the vehicle, the muscle being one of muscles for operating a steering means;

obtaining, based on the acquired time-series myoelectric potential signal, a parameter value representing a fluctuation amount of the myoelectric potential signal and a mean value of the time-series myoelectric potential signal; and evaluating, based on both the parameter value and the mean value, the vehicle such that when the parameter value has a smaller value and the mean value has a smaller value, the drivability of the vehicle is higher, wherein, in obtaining the parameter value, the parameter value is obtained by the calculating unit by using a myoelectric potential signal corresponding to a time during which the vehicle is traveling under a predetermined traveling condition, the predetermined traveling condition comprises a condition that the vehicle travels on a traveling path which at least includes a curved path having a constant curvature, and the traveling path is a path that the vehicle traveled on a straight path, gradually increases a steering angle so as to enter the curved path having the constant curvature, passes through the curved path having the constant curvature, and gradually increases the steering angle so as to again enter on the straight path, wherein, a mean value of the time-series myoelectric potential signal is obtained together with the parameter value; and in evaluating the drivability, an evaluating unit evaluates the vehicle such that when the parameter value has smaller value and the mean value has smaller value, the drivability of the vehicle is higher, based on both the parameter value and the mean value, wherein the parameter value indicates a level of both of frequency and magnitude of steering adjustment made by the driver when driving the vehicle under a predetermined traveling condition, the parameter value comprises at least one of a standard deviation, a dispersion, a distribution range of the time-series myoelectric potential signal, and a root mean square of the waveform obtained by subjecting the information corresponding to the time-series myoelectric potential signal to time differentiation, and the greater parameter value indicates that the driver is making steering adjustments at higher frequency and more greatly.

* * * * *